Sept. 5, 1933. E. E. HARRINGTON Re. 18,939

CATAMENIAL BANDAGE HOLDER

Original Filed Sept. 15, 1928

Inventor

Earl E. Harrington

By Charles B. Mann Jr.

Attorney

Reissued Sept. 5, 1933

Re. 18,939

UNITED STATES PATENT OFFICE 18,939

CATAMENIAL BANDAGE HOLDER

Earl E. Harrington, Washington, D. C., assignor to Max Hain, Los Angeles, Calif.

Original No. 1,730,765, dated October 8, 1929, Serial No. 306,220, September 15, 1928. Application for reissue June 20, 1931. Serial No. 545,796

6 Claims. (Cl. 128—290)

This invention relates to an improved catamenial bandage holder and has for its object to provide an improved pad holder and protector whereby the pad may be held in place on the holder by clamping means of a novel character.

The present invention is a direct improvement on the structure set forth in my Letters Patent No. 1,730,818 dated October 8, 1929 and is directed to the features whereby the clamping tapes which secure the pad to the carrier are operated by lengthwise strain on the opposite ends of the carrier supports.

The invention is illustrated in the accompanying drawing, wherein,—

Figure 1:
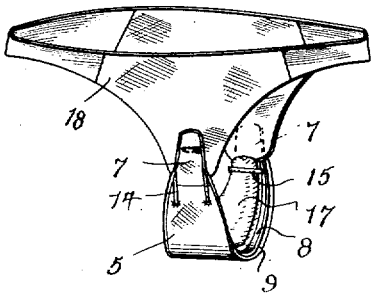
Fig. 1 shows the device in perspective attached to and suspended from a body band.
Figure 2:
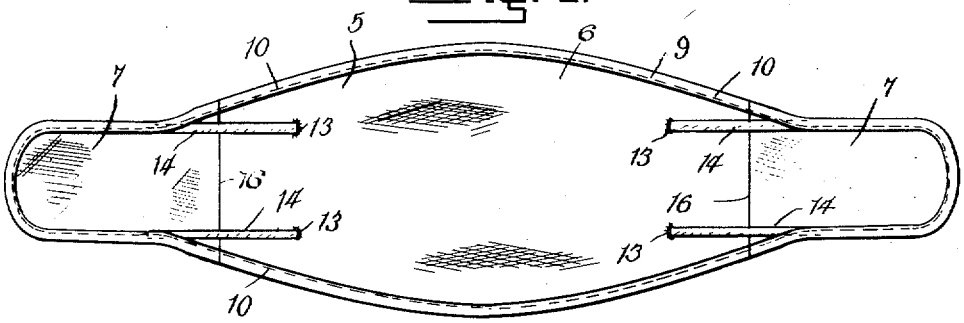
Fig. 2 illustrates the pad holder as viewed from the under side thereof.
Figure 3:
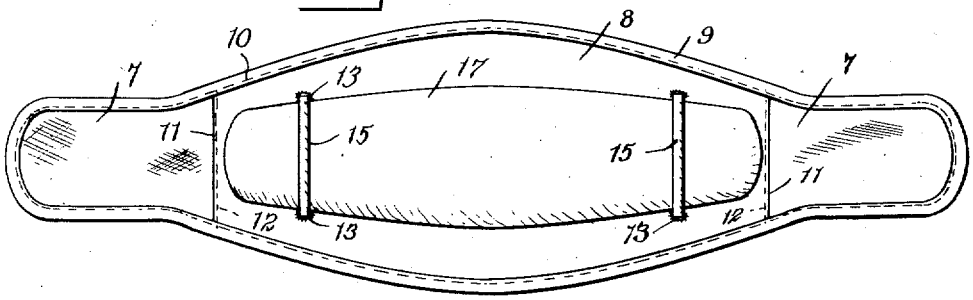
Fig. 3 shows the holder with a pad in place thereon as viewed from the upper side thereof.

In the drawing, the numeral 5 designates a fabric strip having a wide intermediate portion 6 and the narrower tab-like opposite ends 7.

On one side of the wider intermediate portion 6 I provide a sheet or strip of moisture-proof material such as thin rubber 8 and I provide a binding 9 which extends preferably all the way around the fabric strip, which binding engages the longitudinal edges of the two strips 5 and 8 and thus permanently secures those strips together with the rubber strip on top of the fabric strip.

The binding is secured by a continuous row of stitching 10, and the opposite end edges 11 of the rubber strip are secured in a crosswise direction to the fabric strip by rows of stitching 12.

Near each end of the rubber strip 8, but spaced from the end-edges 11 thereof, I provide two perforations 13 which latter extend through both the rubber strip 8 and the fabric strip 5. The perforations are arranged in pairs near each end of the rubber strip, and each perforation of a pair is spaced from the longitudinal side edge of the holder and substantially on a straight line with the tape bound side edges of the tab-like ends 7. There is an advantage in locating the perforations in line with and at the rear of the tape-bound side edges of the end tabs as will presently be pointed out.

The two ends 14 of a tape are passed through the spaced perforations 13 from the upper rubber strip side so that the ends 14 will project at the under side of the fabric strip and thus forms a cross-stretch 15, of the tape over the rubber strip. The two ends 14 of the tape are extended forwardly onto the tab-ends 7 and one tape end is inserted beneath the binding 9 at one longitudinal side-edge of the tab while the other tape end is inserted beneath the binding at the opposite longitudinal side-edge of the tab.

In this way the two tape-ends 14 are permanantly secured to the opposite edges of the tab 7 by the same stitches 10, which secure the binding 9 to the edges of the tab.

Figure 4:
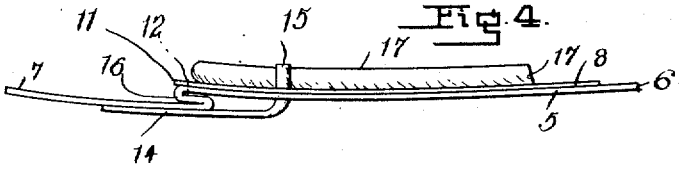
Fig. 4 illustrates an enlarged sectional detail through one end of the holder and the pad thereof with the clamping tape engaging the end of the pad,—the section being taken substantially on the line 4—4 of Fig. 3.

A feature of importance resides in the particular manner in which the tape 14, 15 is applied, for it will be noted that not only do the tape ends 14 extend straight back from the longitudinally-bound side edges of the tabs to the perforations 13, but, the forward ends of this tape are attached to the tab at a point which requires a cross-fold or plait 16 to be made in the fabric strip 5, between the attached ends of the tape and the perforations. This fold 16 is shown in an exaggerated form in Fig. 4 of the drawing and has a special object in view.

It is to be understood that the absorbent pad 17, is placed on the upper rubber strip 8 and that the forward and rear ends of the pad are to be passed beneath the cross-stretch 15 of the tape so that said stretch, when the tape ends are pulled taut, will clamp said pad ends against the rubber strip.

To effect this clamping by the cross-stretch 15, I attach the ends 14 of the tape far enough forward on the tabs 7 and in front of the cross fold or plait 17, so that when the holder is attached to a body belt 18 by the forward ends of its tabs 7, the strain will be transferred through the tape ends back to the cross stretch and this will draw taut across the ends of the pad before the fold or plait 17 can stretch out.

Moreover, the strain is on the reinforced bound side edges of the tabs and then straight back through the tape-ends to the perforations, so that the tabs are kept stretched in a cross-wise direction and the strain is directed longitudinally through the holder at opposite sides of a longitudinal center line.

Having described my invention, I claim,—

1. A catamenial bandage holder comprising a flexible strip on which a pad may be laid said strip having two spaced openings therethrough, a tape extending through said openings from the upper side of the strip and the two ends of the tape extending toward the adjacent end of the holder strip and being attached to said strip-end so as to cause a fullness in the strip between said forward attached ends of the tape and the spaced openings through said strip.

2. A catamenial bandage holder comprising a flexible strip on which a pad may be laid said strip having two crosswise-spaced openings near each end thereof, a tape passed through each pair of openings so as to produce a cross stretch of the tape on the upper side of the strip while the two ends of the tape pass through to the lower side of the strip, said two tape-ends extending toward the adjacent end of the holder strip and being permanently attached thereto,—the strip having a lengthwise fullness between the attached ends of the tape and said openings whereby when the ends of the strip are pulled to take up the fullness the cross-stretch of the tape will be drawn toward the upper side of the strip to clamp a pad thereof.

3. A catamenial bandage holder comprising a flexible strip on which a pad may be laid said strip having its ends somewhat reduced to form tabs, the strip being provided with two spaced perforations adjacent the inner end of each of the tabs, a tape having its two ends passed through said perforations from the upper side of the strip so that the ends of the tape will project on the under side of the strip said tape-ends extending from said perforations toward the adjacent tab-end of the holder and the holder being folded crosswise under the tape-ends whereby to produce a fullness in the holder and to draw the intermediate part of the tape against the upper side of the strip.

4. A carrier comprising a flexible strip for supporting a pad, a tape having a portion movably mounted in respect to said strip and adapted to embrace the pad, a portion of said strip forming a supporting means for the carrier, said tape having a lengthwise fullness and connection with said strip supporting means and binding the pad on the carrier when strain is placed on the strip support to remove the lengthwise fullness when strain is placed upon the same when in position upon a wearer.

5. A device of the character described, comprising a strip on which a pad may be laid, a movable cord for embracing said pad, a portion of said strip providing a strip supporting means, said cord attached to said strip supporting means to form in said means a fullness intermediate the length of the cord, and said fullness being taken up and said cord binding the pad on the strip when strain is placed upon the strip supporting means.

6. A device of the kind described comprising a carrier for supporting a pad, supporting means for the carrier adapted to have a cross fold, a cord having a portion movably mounted in respect to said carrier and having a connection with said supporting means for binding a pad upon said carrier, said cord being adapted to embrace and bind the pad upon the carrier when strain is placed upon the supporting means and the cross fold of the carrier is taken up when in position upon a wearer.

EARL E. HARRINGTON.